(12) United States Patent
West et al.

(10) Patent No.: US 10,398,525 B1
(45) Date of Patent: Sep. 3, 2019

(54) MEDICAL MONITOR POUCH

(71) Applicants: Colin L. West, King George, VA (US); Kelcy L. Seabolt, Leonardtown, MD (US); Philip Frank Heffner, Woodford, VA (US)

(72) Inventors: Colin L. West, King George, VA (US); Kelcy L. Seabolt, Leonardtown, MD (US); Philip Frank Heffner, Woodford, VA (US)

(73) Assignee: United States of America, as represented by the Secretary of the Navy, Arlington, VA (US)

( * ) Notice: Subject to any disclaimer, the term of this patent is extended or adjusted under 35 U.S.C. 154(b) by 0 days.

(21) Appl. No.: 16/157,146

(22) Filed: Oct. 11, 2018

(51) Int. Cl.
- B65D 85/38 (2006.01)
- A61B 50/30 (2016.01)
- A61G 1/04 (2006.01)
- A61B 50/00 (2016.01)

(52) U.S. Cl.
CPC ............. *A61B 50/30* (2016.02); *A61G 1/04* (2013.01); *A61B 2050/005* (2016.02); *A61B 2050/3008* (2016.02); *A61B 2050/3015* (2016.02); *A61B 2050/314* (2016.02)

(58) Field of Classification Search
CPC ............ A61B 50/30; A61B 2050/314; A61B 2050/005; A61B 2050/3008; A61B 2050/3015; A61G 1/04; A45C 2011/002; A45C 2011/003; B65D 85/38
USPC ...... 206/305, 320, 316.2, 316.3; 383/40, 38, 383/106
See application file for complete search history.

(56) References Cited

U.S. PATENT DOCUMENTS

| | | | | |
|---|---|---|---|---|
| 4,213,549 | A * | 7/1980 | Hibbard | A45C 11/22 224/153 |
| 5,316,388 | A * | 5/1994 | Caligiuri | A45C 11/20 383/127 |
| 5,873,456 | A * | 2/1999 | Hull | H01H 9/0242 206/305 |
| 6,347,796 | B1 * | 2/2002 | Grossman | A63F 13/02 273/148 B |
| 2002/0014420 | A1 * | 2/2002 | Schultz | B65D 85/38 206/305 |
| 2002/0088726 | A1 * | 7/2002 | Chou | A45F 3/04 206/320 |
| 2009/0118576 | A1 * | 5/2009 | Akagi | A61B 1/04 600/109 |
| 2009/0184014 | A1 * | 7/2009 | Lee | A45C 13/02 206/320 |
| 2012/0048900 | A1 * | 3/2012 | Wong | A45C 3/001 224/257 |

* cited by examiner

*Primary Examiner* — Rafael A Ortiz
(74) *Attorney, Agent, or Firm* — Gerhard W. Thielman

(57) ABSTRACT

A bag is provided for a medical monitor attachable to a litter. The bag includes a housing satchel, an upper cowl, a harness, and first and second flaps. The upper cowl closes an upper opening through which the satchel receives the monitor. The first flap connects to a front side of the satchel from a bottom edge and secures at a top edge by detachable buttons. The first flap includes a window for viewing the monitor. The second flap connects to the first flap to reversibly cover the window. The harness attaches the satchel to the litter. The satchel further includes a utility pocket connected to the satchel at a bottom edge and flexible for rolling underneath the satchel.

6 Claims, 16 Drawing Sheets

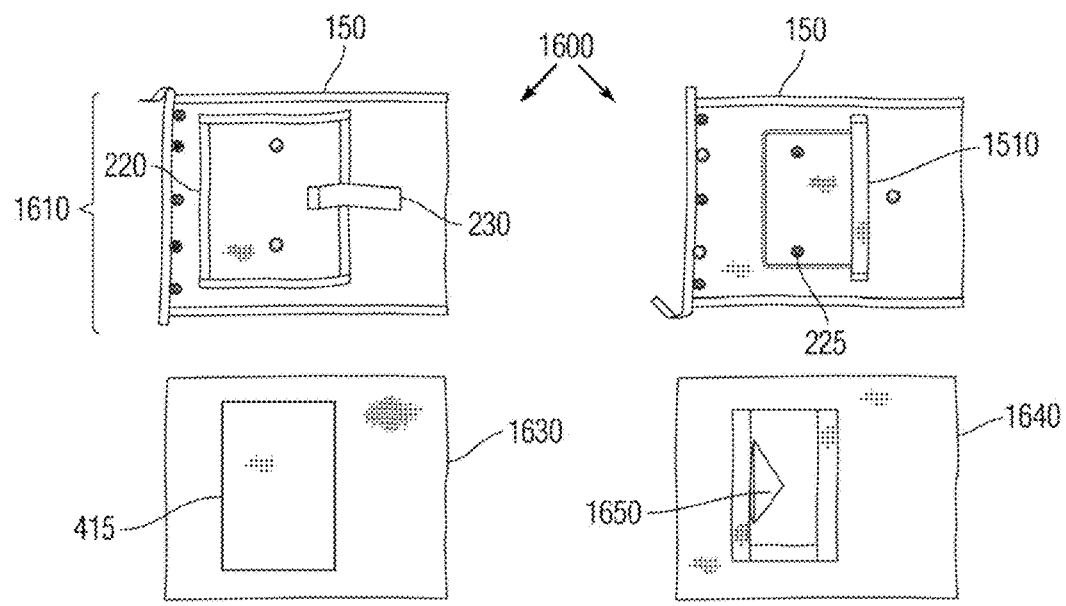
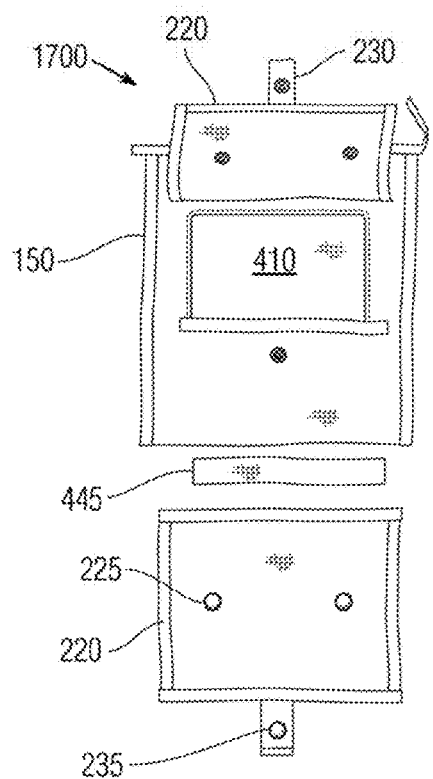
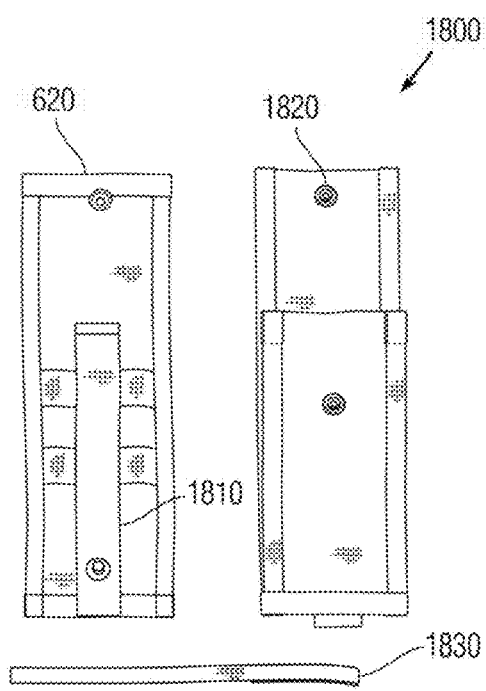
Fig. 16
Fig. 17
Fig. 18

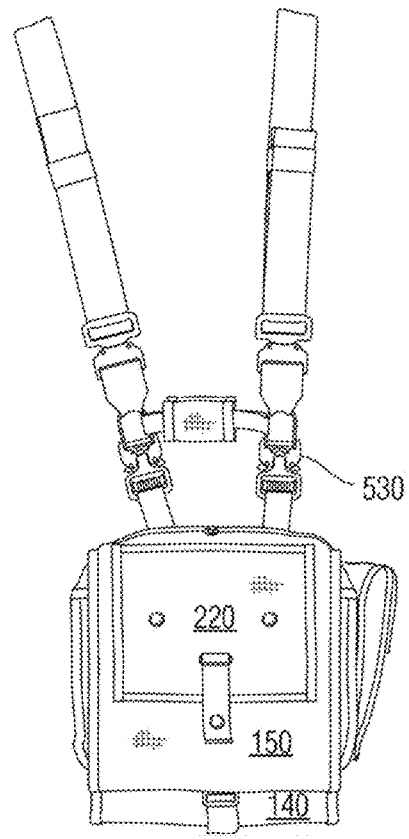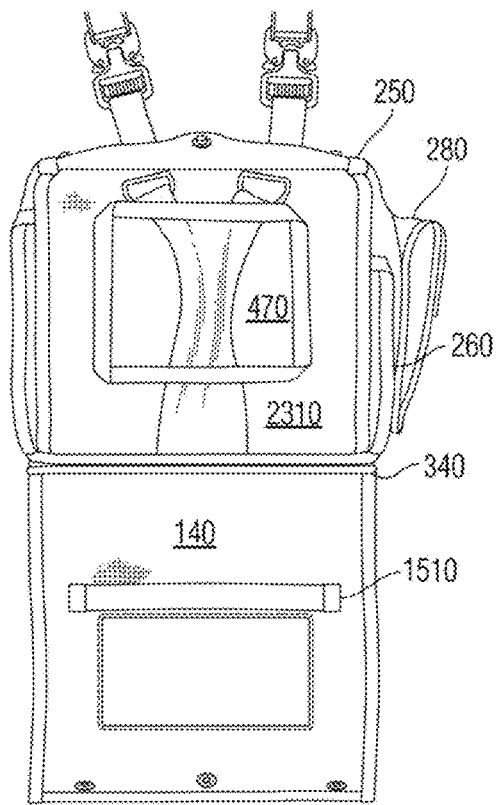
Fig. 23A    Fig. 23B
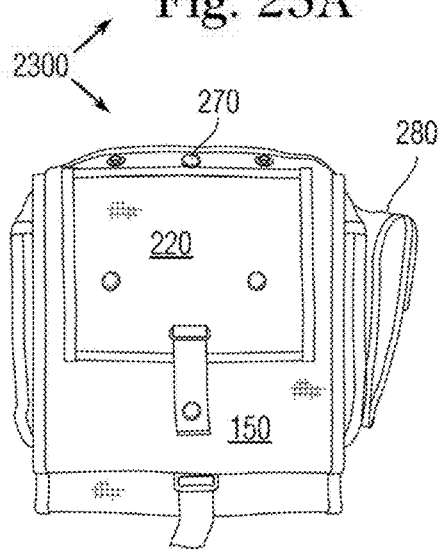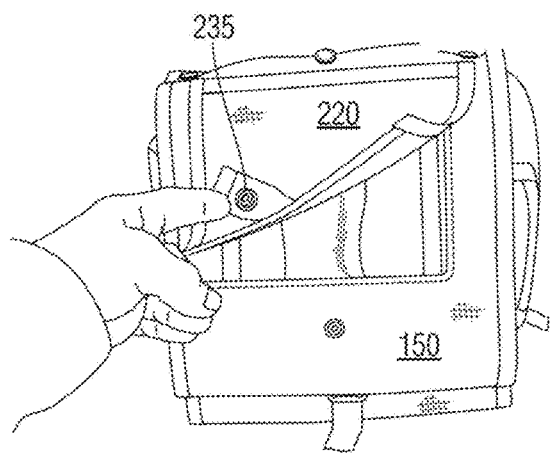
Fig. 23C    Fig. 23D

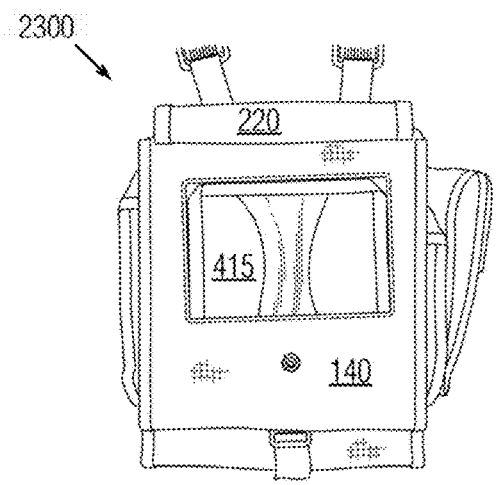
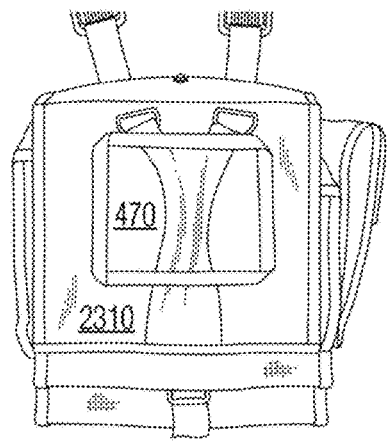
Fig. 23E  Fig. 23F
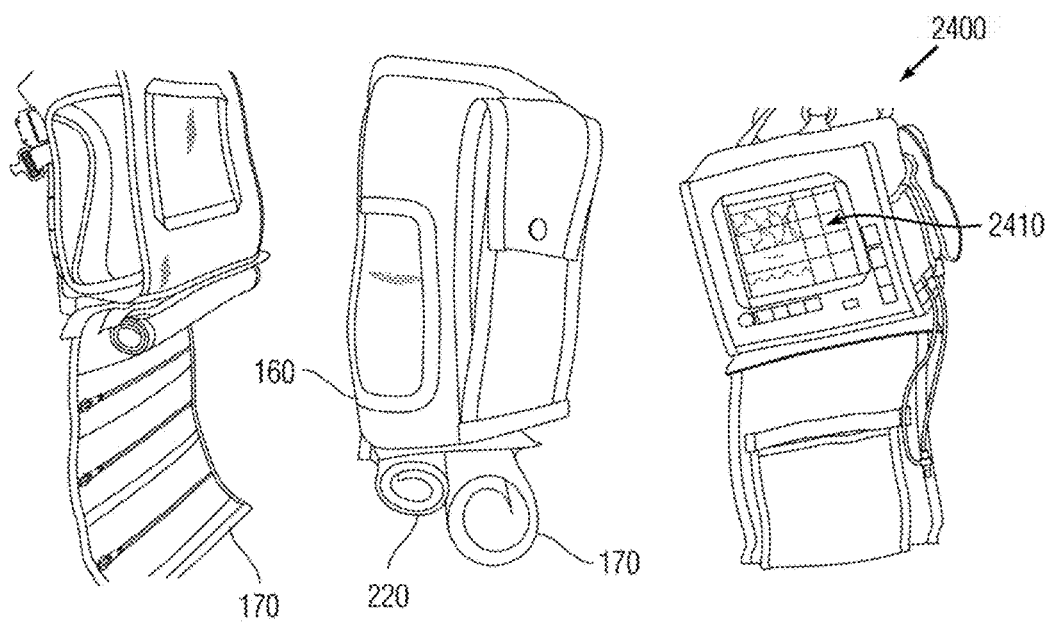
Fig. 24

MEDICAL MONITOR POUCH

STATEMENT OF GOVERNMENT INTEREST

The invention described was made in the performance of official duties by one or more employees of the Department of the Navy, and thus, the invention herein may be manufactured, used or licensed by or for the Government of the United States of America for governmental purposes without the payment of any royalties thereon or therefor.

BACKGROUND

The invention relates generally to a portable pouch secured to a gurney for containing a medical monitor. In particular, the invention relates to a flexible container that enables the monitor to interactively operate and provide visual information for medical personnel while being transported.

Following United States Navy efforts to reduce battlefield Killed in Action (KIA) the Marine Corps Warfighting Laboratory (MCWL) advocates for a strategy to combine technology and doctrine to provide a higher standard level of medical care pushed further forward towards the edge of battle. The "golden hour" is a generally accepted term by emergency medical providers that references the hour (or less) immediately following a traumatic injury to a casualty. Advanced medical care provided by emergency room surgeons within the golden hour greatly reduces mortality.

Recent military doctrine emphasizes a shift away from elaborate and expensive ground-based operations and focusing on sea-based solutions. The Expeditionary Force-21 (EF-21) concept envisions the future force to deploy faster, lighter, and further forward, with a heavy reliance on littoral operations and technology to support the precision fighting of an agile and diverse force. The EF-21 tenets significantly influence medical requirements and capabilities necessary to support the future fight, requiring a smaller medical footprint, landing lighter equipment loads and highly reliant on medical resupply.

Consequently, medical treatment facilities will be required to hold casualties for longer periods of time prior to evacuation. When evacuation is available, the flight times may be longer, potentially requiring medical intervention in flight. This shift negatively affects the likelihood of a casualty reaching definitive care within the golden hour. To combat the effects of the increase in medical evacuation times, advanced medical equipment is being pushed further towards the point of injury (POI), specifically ruggedized patient monitors. The TEMPUS Prom from Remote Diagnostics Technologies LLC in Huntsville, Ala. represents one such example of a portable monitor. See https://az767150.vo.msecnd.net/pdf/RDT_Tempus_Pro_Brochure.pdf.

Ruggedized medical monitors shift many traditional emergency room capabilities closer to the POI, for instance monitoring blood pressure, heartrate and oxygen saturation, and conducting medical exams such as ultrasound. For operation from POI to definitive care in a hospital, medical monitors need to facilitate ancillary equipment, provide extra utility to caregivers, and enable safe deployment during ground/air vehicle based evacuations. To fully support the EF-21 concept, medical monitoring equipment must be easily moved on and off the evacuation vehicle and effectively utilized while during movement, both in-flight and on the ground.

SUMMARY

Conventional medical equipment packages yield disadvantages addressed by various exemplary embodiments of the present invention. In particular, various exemplary embodiments provide a pouch for containing medical equipment on a litter. Exemplary embodiments provide a bag for a medical monitor attachable to a litter. The bag includes a housing satchel, an upper cowl, a belt, and first and second flaps. The upper cowl closes an upper opening through which the satchel receives the monitor. The first flap connects to a front side of the satchel from a bottom edge and secures at a top edge by detachable buttons. The first flap includes a window for viewing the monitor. The second flap connects to the first flap to reversibly cover the window. The belt attaches the satchel to the litter. In additional embodiments, the satchel includes a utility pocket connected to the satchel at a bottom edge and flexible for rolling underneath the satchel.

BRIEF DESCRIPTION OF THE DRAWINGS

These and various other features and aspects of various exemplary embodiments will be readily understood with reference to the following detailed description taken in conjunction with the accompanying drawings, in which like or similar numbers are used throughout, and in which:

FIG. 16 is a set of perspective views of the flap viewing window;

FIG. 17 is a set of perspective views of the flap viewing window;

FIG. 18 is a perspective view of the external attachments;

FIGS. 23A through 23F are perspective views of the bag and medical monitor;

FIG. 24 is a set of perspective views of the bag as deployed and a medical monitor housed therein.

DETAILED DESCRIPTION

In the following detailed description of exemplary embodiments of the invention, reference is made to the accompanying drawings that form a part hereof, and in which is shown by way of illustration specific exemplary embodiments in which the invention may be practiced. These embodiments are described in sufficient detail to enable those skilled in the art to practice the invention. Other embodiments may be utilized, and logical, mechanical, and other changes may be made without departing from the spirit or scope of the present invention. The following detailed description is, therefore, not to be taken in a limiting sense, and the scope of the present invention is defined only by the appended claims.

Medical monitors offer a multitude of tools for measuring and gauging a patient's condition. While these devices are ruggedized, they are not ideally packaged for use in the field by most Military Occupation Specialties (MOS) and are not certified for flight operations. Naval Surface Warfare Center—Dahlgren Division (NSWCDD) H14 Branch and support contractors have designed a solution that enables field deployment of medical monitors.

The exemplary Air Certified Medical Monitor Strategic Pouch turns the medical monitor and ancillary equipment into a versatile and configurable single package that is also certified for use during aviation evacuations. The exemplary bag enables ready access to connections for medical leads as well as access to data, power, and control ports. The touch screen can be covered for additional protection during movement, or uncovered for operations. All hard buttons are visible and accessible through a clear plastic covering.

The exemplary design incorporates MOdular Lightweight Load-carrying Equipment (MOLLE) webbing to enable the incorporation of additional pouches to accommodate operational needs. This design feature affords a high level of customizable configurations to fulfill unit/mission specific requirements. An add-on pouch is attached to the bottom of the Medical Monitor Strategic Pouch that enabling several sets of sterile medical leads to be accessed as new patients are connected to the monitor to prevent contamination between patients. The monitor bag enables the medical monitoring device to be safely mounted for use in all environments including airframes providing for truly complete monitoring from POI to final destination.

Figure 1:
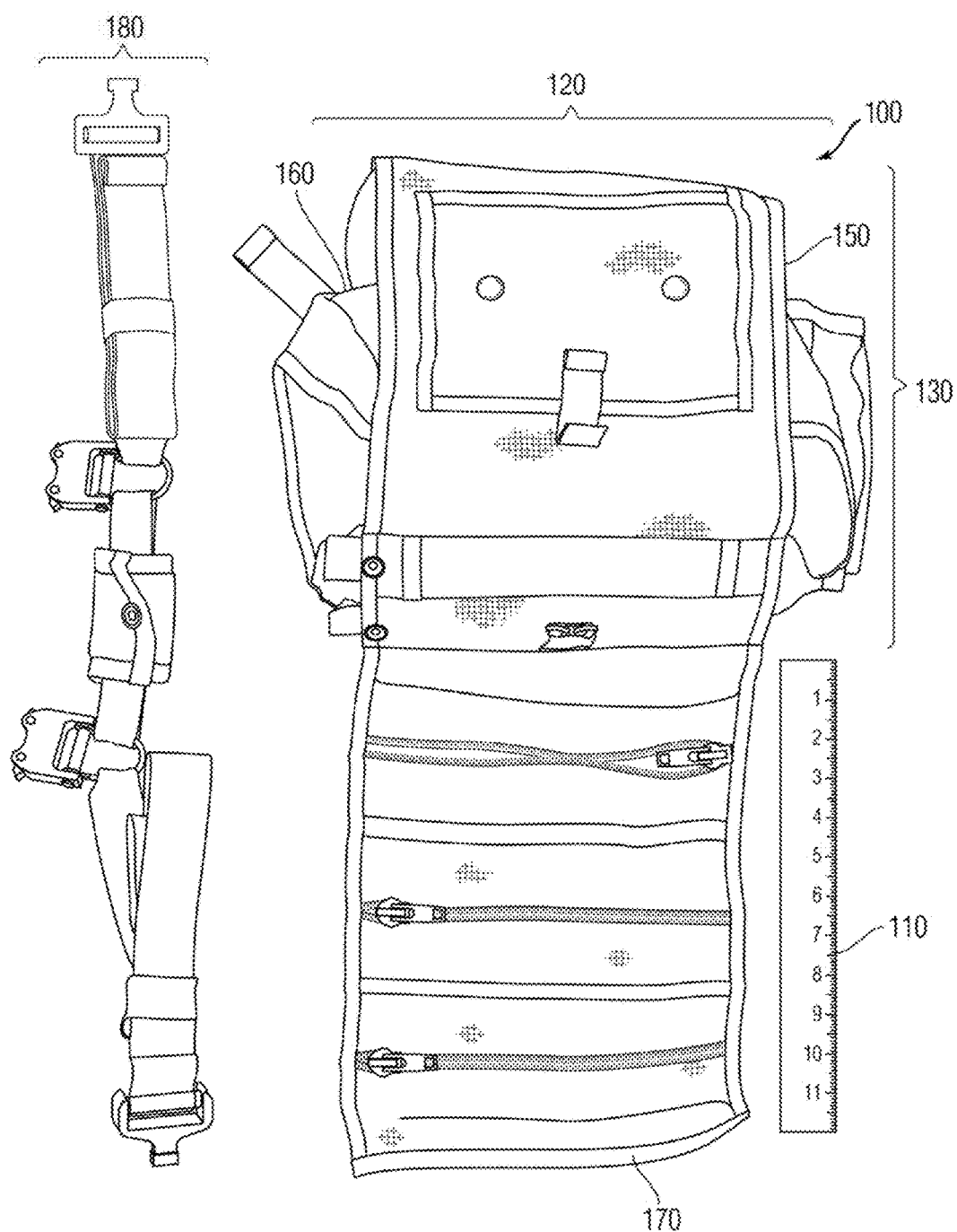
FIG. 1 is a perspective view of an exemplary bag and harness straps.

FIG. 1 shows a perspective view 100 with a ruler 110 for length scale of an exemplary bag 120 from its obverse face, which includes a housing satchel 130 for containing a medical monitor. An inner front flap 140 provides a front face for a medical monitor. An outer front flap 150 attaches to the inner flap 140, and a monitor cowl 160 is disposed behind the inner flap 140. The bag 120 also includes a utility pocket 170 that hangs from the satchel 130. The pocket 170 can contain sundry medical items in zippered mesh enclosures. The view 100 also shows a belt harness 180.

The housing satchel 130 provides a soft container (whose volume is defined by the cowl 160) for the monitor with which to measure and/or treat a patient's conditions. The exemplary bag 120 is approximately twelve inches wide, eight inches high and four inches deep and can be composed of heavy-duty Nylon and may include a camouflage printed surface. The harness 180 passes through the housing satchel 130 and hangs from a bar of the litter or gurney to support the monitor. Instrumentation cables connect the monitor to sensors attached to the patient on the litter. The monitor can be, for example, a TEMPUS Pro model. The associated properties are exemplary only and not limiting.

Figure 2:
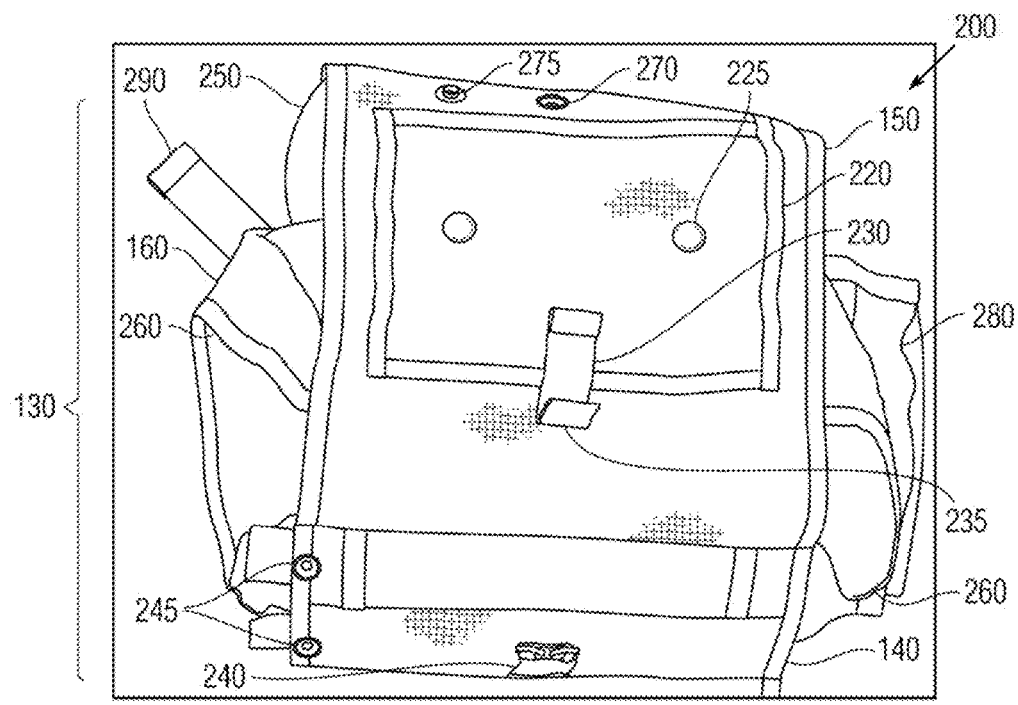
FIG. 2 is a perspective view of a housing satchel.

FIG. 2 shows a perspective view 200 of the exemplary satchel 130. A window flap 220 with snap buttons 225 attaches to the outer flap 150 and secured thereto by a tab 230 and associated snap button 235. A latch 240 protrudes between the inner flap 140 and the pocket 170, and lower snap buttons 245 are disposed at the left side. An upper cowl 250 and a lateral enclosure (as side window) 260 extend behind the inner flap 140, the latter including the monitor cowl 160. The outer flap 150 also includes upper snap buttons 270 and 275 (respectively female and male) along the upper periphery. To lift and secure the window flap 220, an operator can raise the tab 230 and secure its male snap button 235 to the female snap button 270. A detachable side pocket 280 can be secured to straps 290 on the reverse face of the satchel 130. The snap buttons 270 and 275 depicted form concentric ring fasteners, although embodiments permit alternative fasteners.

Figure 3:
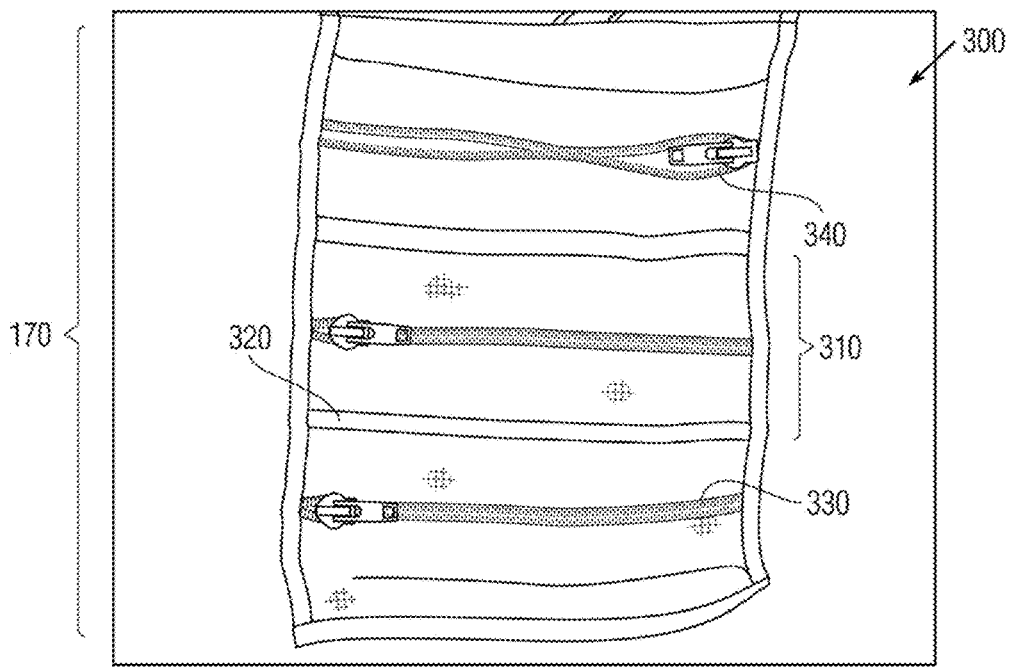
FIG. 3 is a perspective view of a utility pocket.

FIG. 3 shows a perspective view 300 of the exemplary pocket 170 that hangs from the satchel 130. The pocket 170 includes rectangular envelopes 310 separated from each other by horizontal seams 320. Each envelope 310 can be opened and closed along horizontal zippers 330 by pulling a clasp 340. The obverse face of the pocket 170 incorporates MOLLE webbing.

Figure 4A:
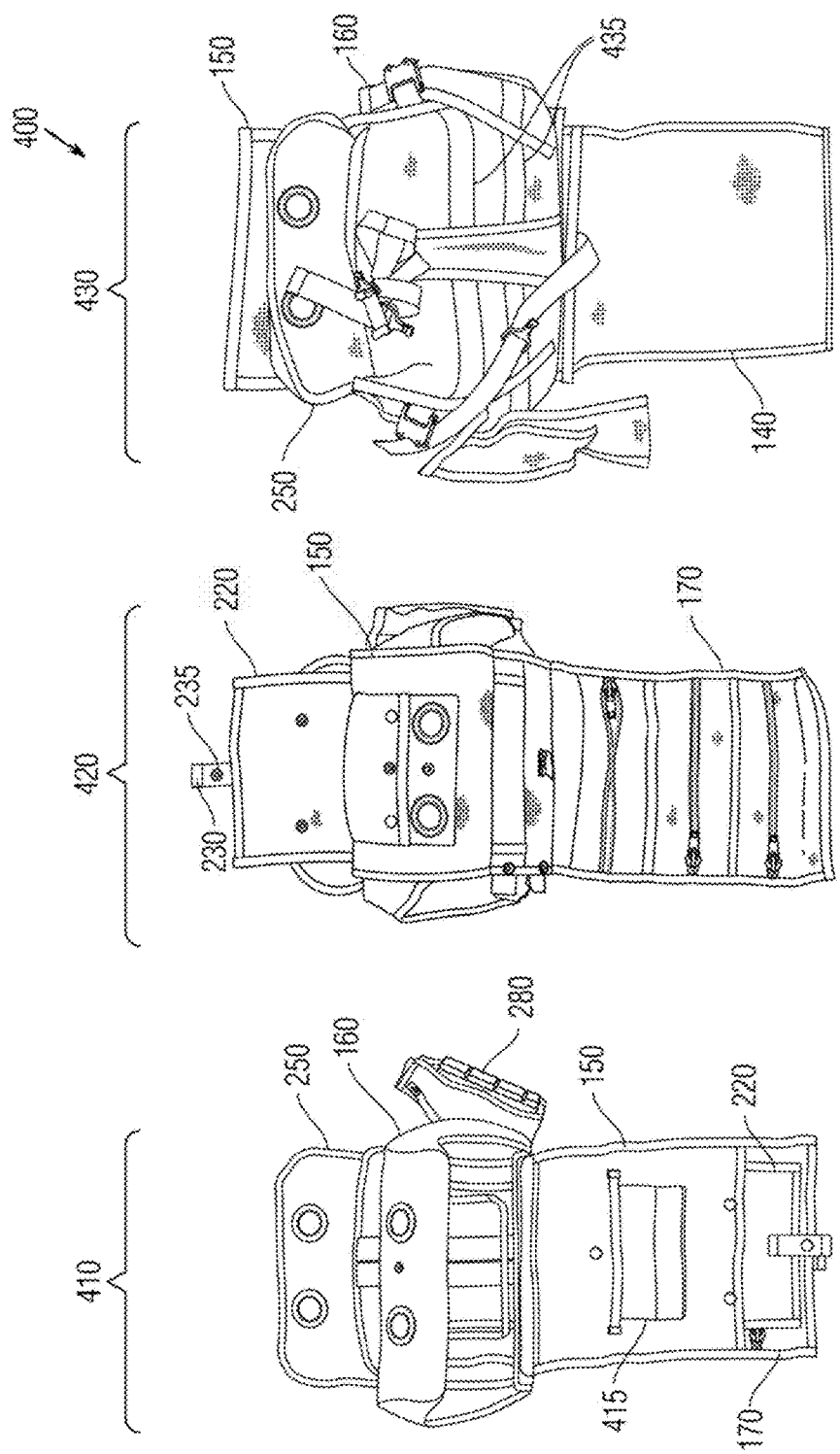
FIGS. 4A and 4B are perspective views of the exemplary bag.
Figure 4B:
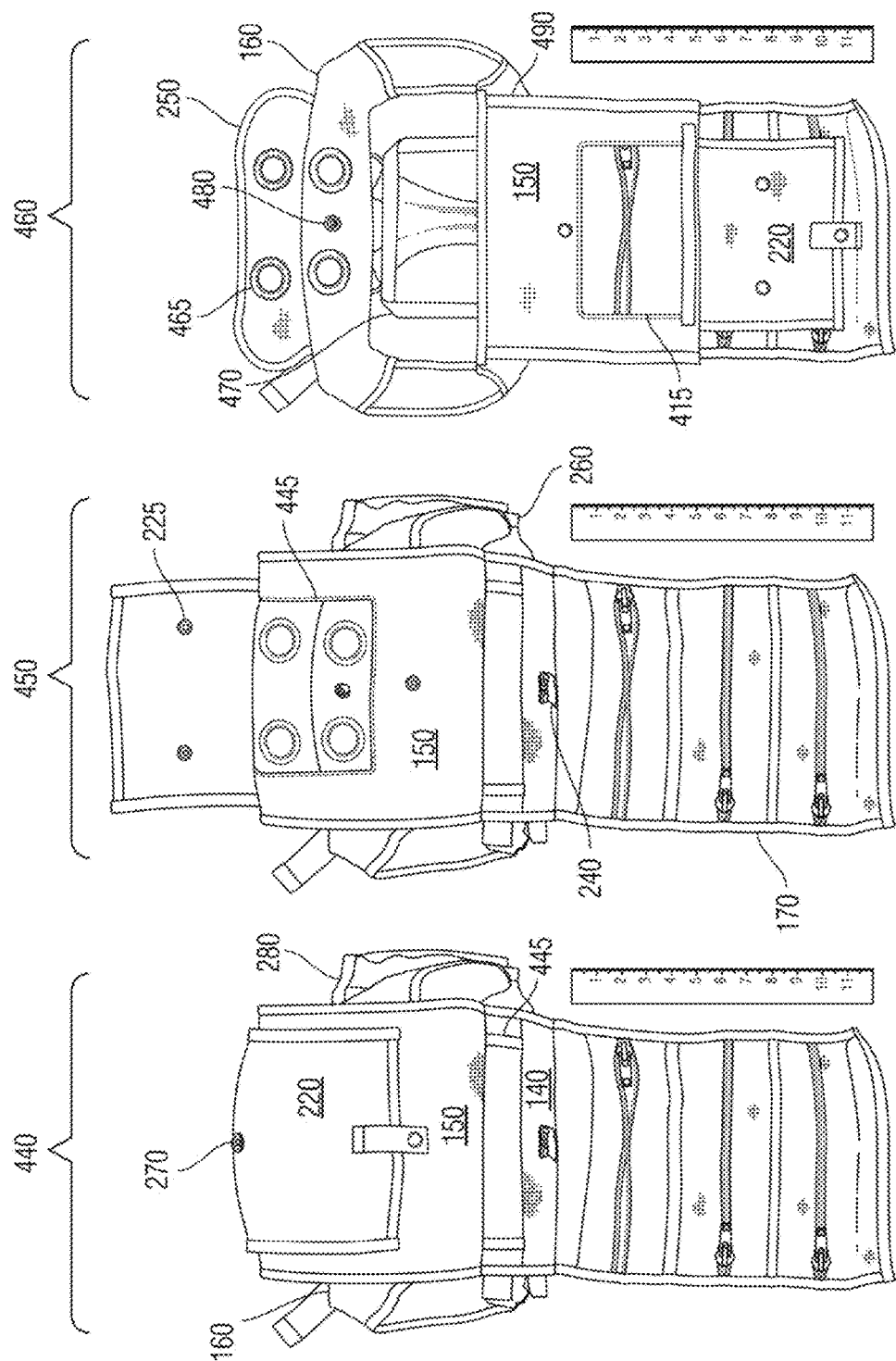
Figure 5A:
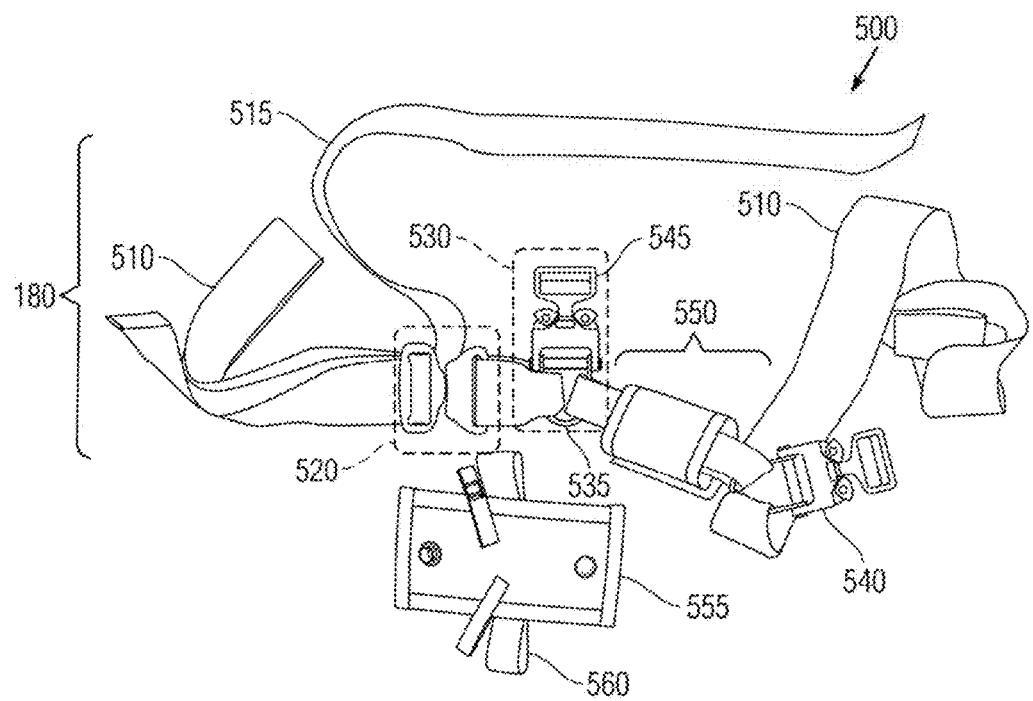
FIGS. 5A and 5B are perspective views of the harness strap.
Figure 5B:
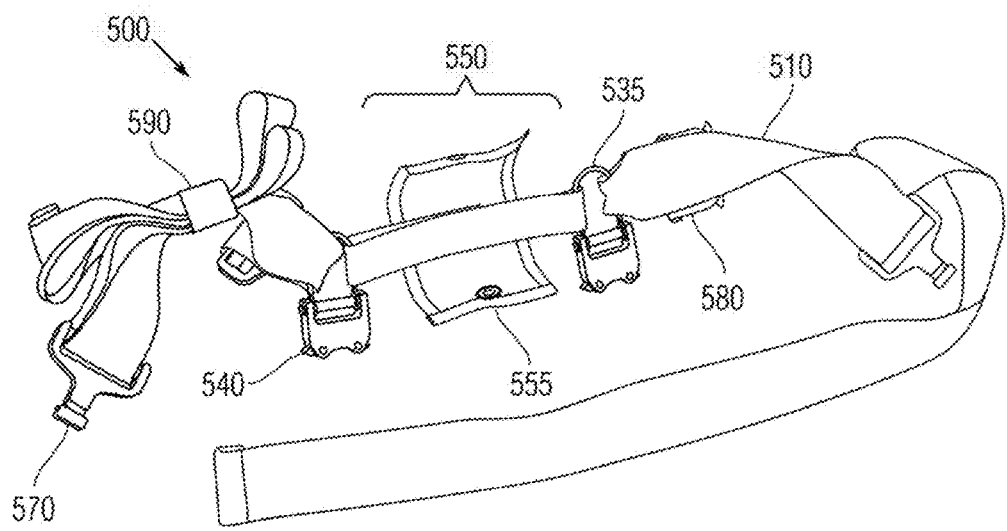

FIGS. 4A and 5B show perspective views 400 of the bag 120 from obverse and reverse sides. The first left view 410 shows the obverse face with the upper cowl 250 lifted and the outer flap 150 lowered over the pocket 170 to reveal the cowl 160. The outer flap 150 includes a rectangular window 415 that can be covered by the window flap 220. The first center view 420 shows the obverse face with the window flap 220 lifted to reveal the cavity in which the monitor can be inserted. The first right view 430 shows the reverse face with the outer flap 150 lifted, the inner flap 140 lowered and the cowl 160 exposed. The reverse face of the cowl 160 includes MOLLE straps 435 for attaching auxiliary pouches. The first optional pouch 280 attaches to straps on the satchel 130 for carrying auxiliary medical items.

The second left view 440 shows the obverse face of the bag 120 similar to view 100, including a MOLLE strap 445. The second center 450 shows the obverse face of the bag 120 with the window flap 220 raised. The monitor cowl 160 includes a horizontally arranged pair of grommets 455 visible through the window 415. The second right view 460 shows the obverse face of the bag 120 with the outer flap 150 lowered to partly obscure the pocket 170 similar to view 410. The upper cowl 250 includes a horizontally arranged pair of grommets 465, parallel to the pair of grommets 455. The monitor cowl 160 includes a window 470 for visible and tactile access to the monitor, with a male snap button 480 above and through which a MOLLE ventilation spine 490 at the rear of the cowl 160 can be observed. The satchel 130 enables a monitor to be inserted through the top of the cowl 160, upon lifting away the upper cowl 250.

FIGS. 5A and 5B show perspective views 500 of the exemplary harness 180, including a pair of straps 510 and an auxiliary tie-down ribbon 515. Each strap 510 connects via belt latch 520 to a clip latch 530 with a loop 535. The clip latch 530 includes a female clevis 540 and a male tang 545. A flexible bridge 550 connects a pair of separate clip latches 530 via their loops 535. The bridge 550 includes a wrap 555 and a strap 560. Each belt latch 520 includes a male prong 570 and a female receiver 580. A press release detaches the receiver 580 from the prong 570. The straps 510 can be restrained by a wrap ring 590.

Figure 6:
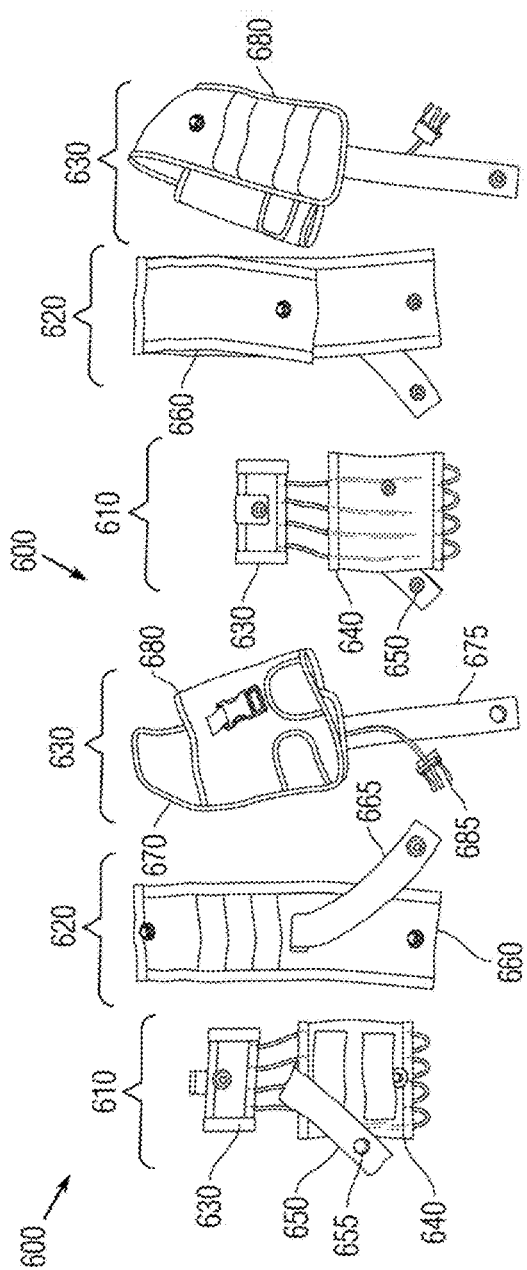
FIG. 6 is a set of perspective views of external attachments.

FIG. 6 shows perspective obverse and reverse views 600 of optional pouches 610, 620 and 630 that can connect to various straps 435 on the satchel 130, or on the harness 180. A second optional pouch 610 for securing a notepad includes a notepad envelope 630 and a pocket 640 having a strap 650. The notepad envelope 630 and strap 650 connect to each other by snap buttons 655. The third optional pouch 620 includes a folding retainer 660 with a strap 665. The fourth optional pouch 630 includes a toolkit holster 670 secured by a strap 675. The pouch 630 also includes a holster 680 and a flexible clip 685.

Figure 7:
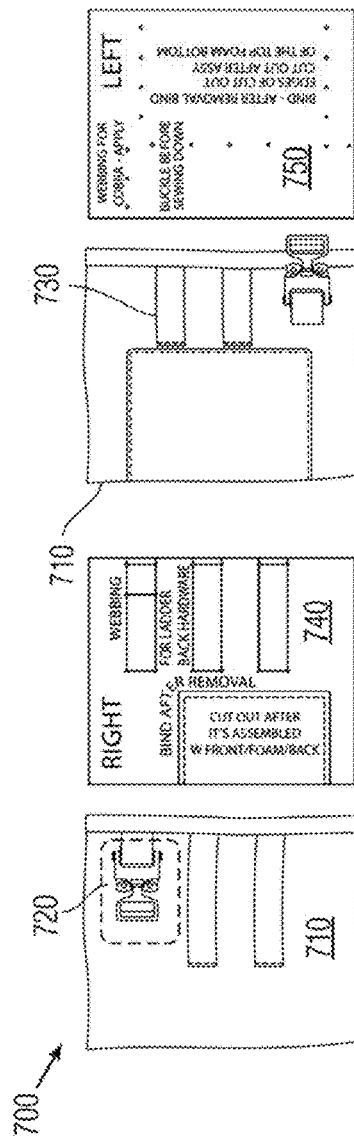
FIG. 7 is a set of perspective views of right and left rear structural panels.

FIG. 7 shows perspective obverse and reverse views 700 of right and left rear structural panels 710 of the satchel 130 with a latch 720 at one edge and straps 730 attached to the flat surface for attaching pouches, e.g., 610, 620 and 630. A plastic template with right 740 and left 750 faces provides a reinforcement backing to ensure stiffness of the rear panels 710.

Figure 8:
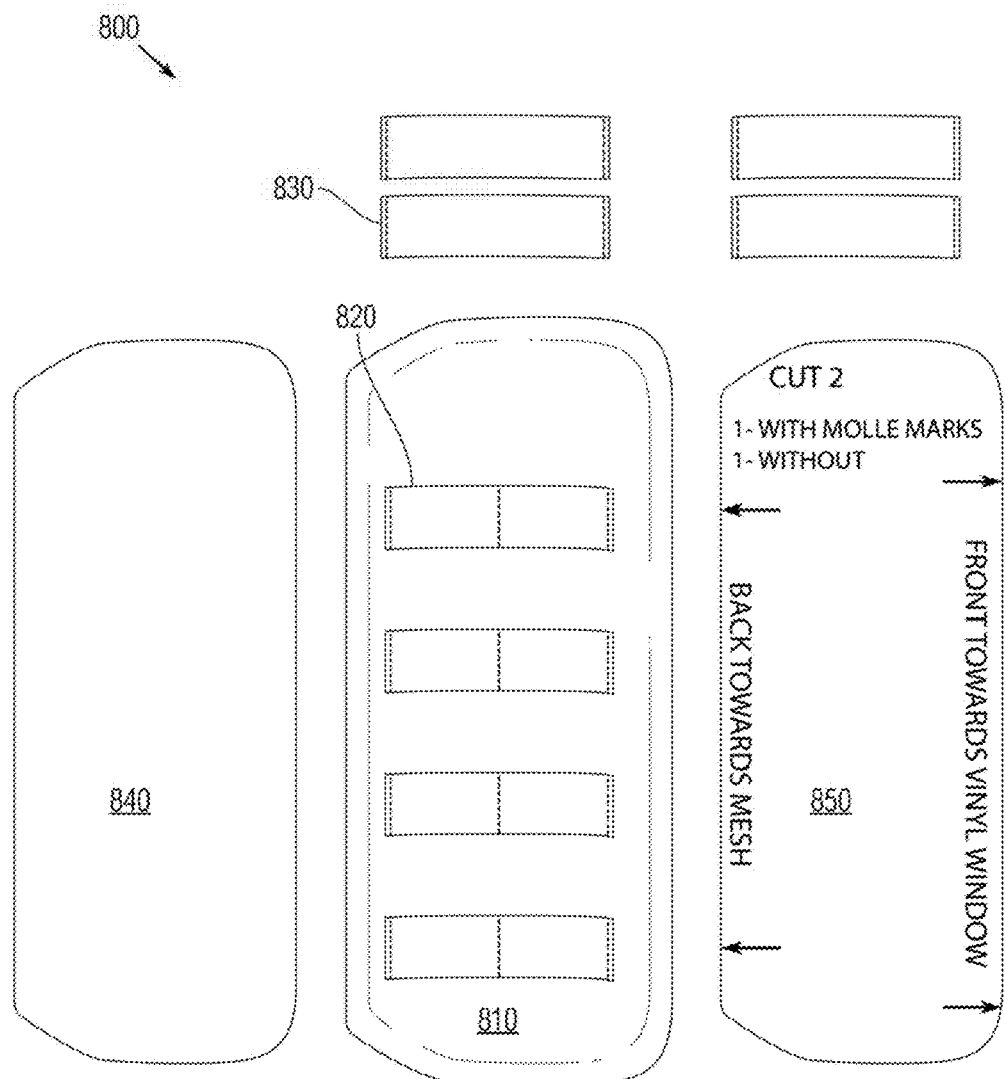
FIG. 8 is a perspective view of a bottom connecting panel.
Figure 9A:
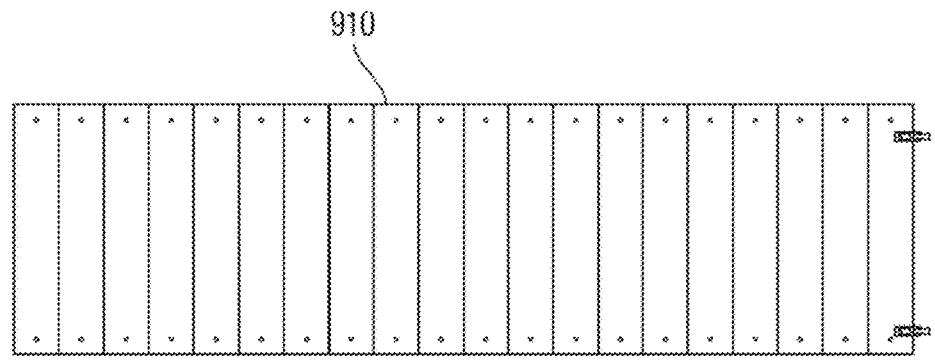
FIGS. 9A and 9B are perspective views of roll-out pouches.
Figure 9B:
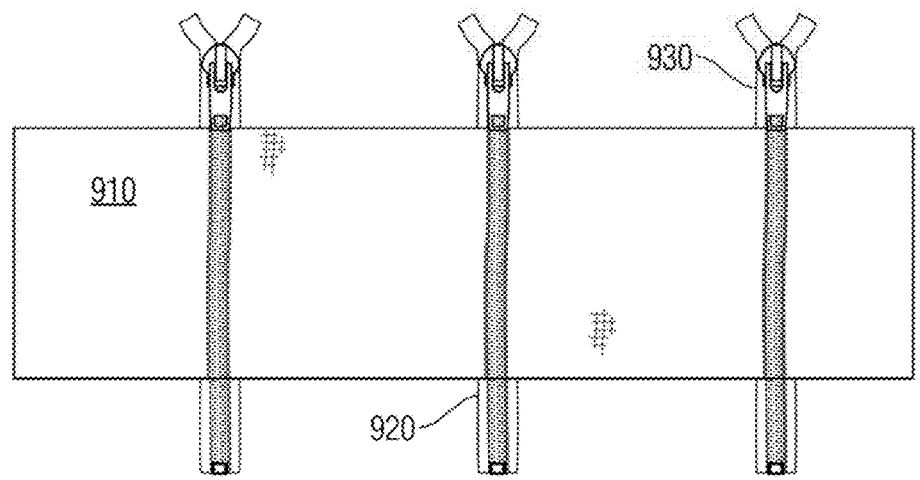

FIG. 8 shows a perspective view 800 of a bottom connecting panel 810 including straps 820 composed of sewn tabs 830. A foam case 840 contains a plastic template 850 inserted therein to provide structural rigidity to the bottom panel 810. FIGS. 9A and 9B show perspective views 900 of a MOLLE strip 910 for roll-out pouches and accompanying zippers 920 sewn thereto, together with their clasps 930 for opening and closing. The MOLLE mesh enables ventilation of the utility pocket 170 and satchel 130.

Figure 10:
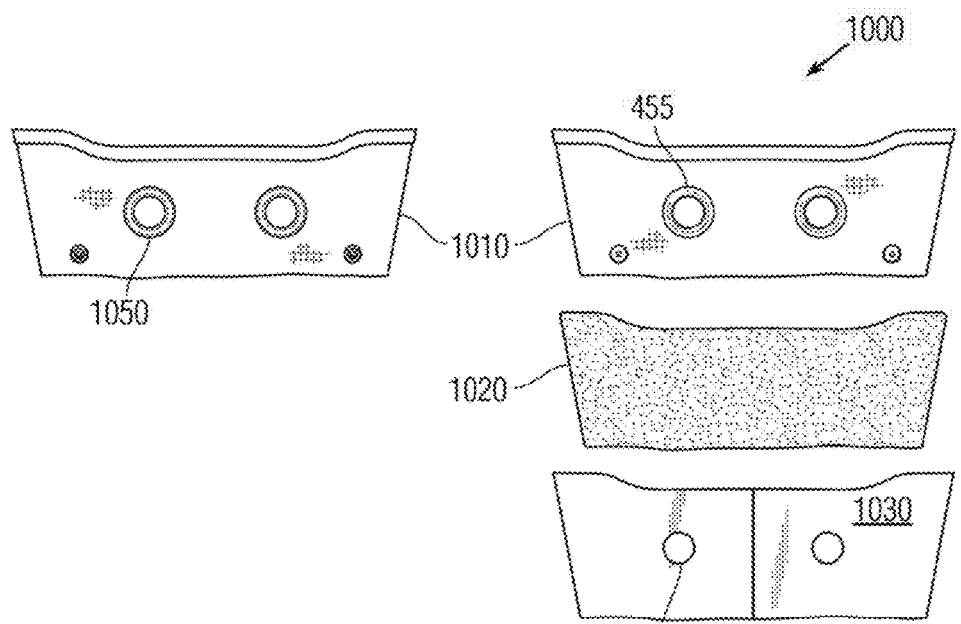
FIG. 10 is a perspective view of an outer cowl flap and template.
Figures 11, 12:
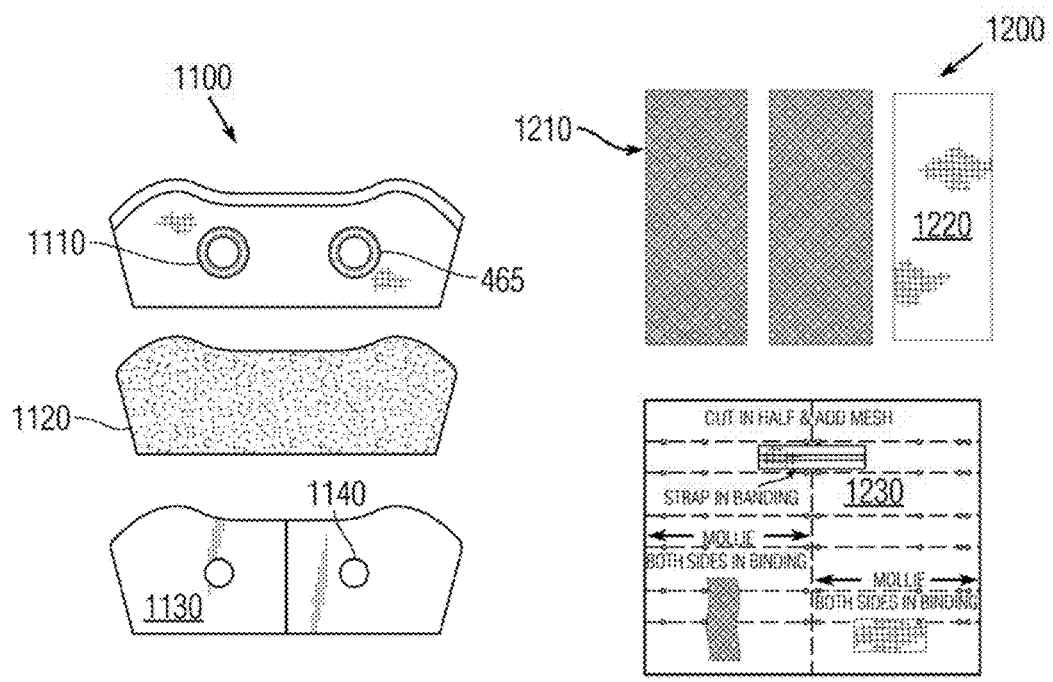
FIG. 11 is a perspective view of an inner cowl flap and template.
FIG. 12 is a perspective view of mesh fabric.

FIG. 10 shows a perspective view 1000 of an outer cowl flap and template 1010 for the monitor cowl 160 and including the abreast pair of grommets 455. The cowl flap 1010 includes a foam pocket 1020 that receives an insert 1030 with aligned holes 1040 aligned with their associated grommets 455 with reverse faces 1050. FIG. 11 shows a perspective view 1100 of an inner cowl flap and template 1110 for the upper cowl 250 and is constructed similarly to the outer cowl flap 1010 and with similar grommets 465. The belt straps 510 pass through the grommets 455 and 465. FIG. 12 shows a perspective view 1200 of mesh fabric 1210 composed of MOLLE webbing. The dimensions are based on plastic templates 1220 and 1230.

Figure 13:
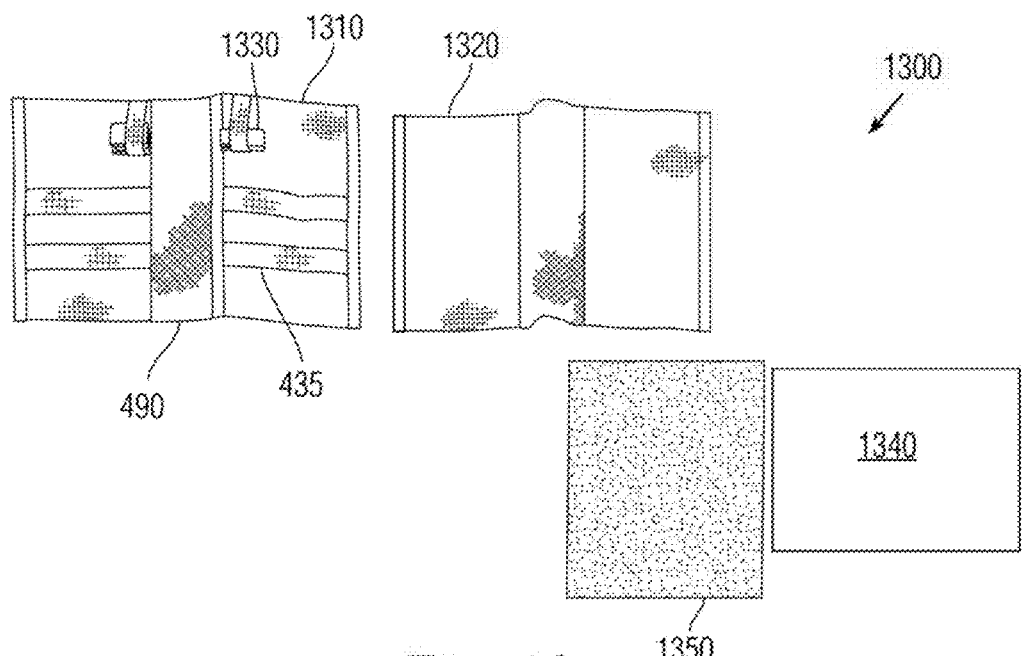
FIG. 13 is a set of perspective views of a rear enclosing panel.

FIG. 13 shows perspective obverse and reverse views 1300 of a rear enclosing panel 1310 (external to the structural panel 710) and its lateral edge strip 1320. The web spine 490 of the cowl 160 enables the enclosing panel 1310 to fold, and the MOLLE straps 435 facilitate disposition of attachment pouches and a latch 1330. Formation of the enclosing panel 1310 includes production of a foam case 1340 and a plastic template 1360 to maintain rigidity.

Figures 14, 15:
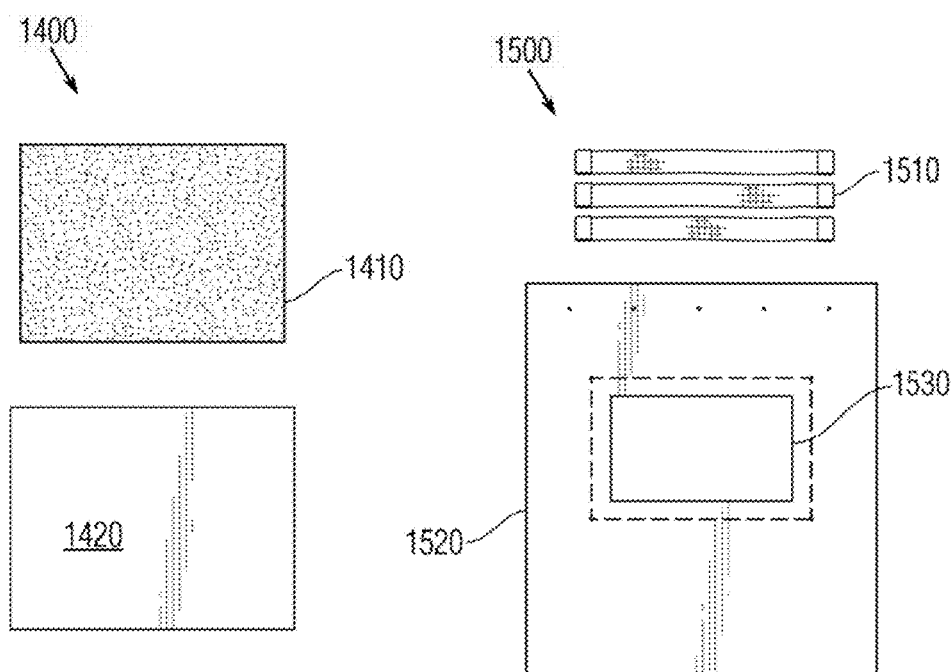
FIG. 14 is a perspective view of window material.
FIG. 15 is a perspective view of a stencil template for cutting a viewing window behind the flap.

FIG. 14 shows a perspective view 1400 of a clear panel 1410 and its sizing template 1420. The panel 1410 is composed of flexible transparent polymer material. FIG. 15 shows a perspective view 1500 of a window template for the outer flap 220. Straps 1510 can be attached to the flap 220 based on a plastic template 1520 having a rectangular cutout 1530 cut out therefrom.

FIG. 16 shows obverse and reverse perspective views 1600 of a window assembly 1610 for the outer flap 150. A strap 1510 is disposed on the reverse face. An obverse facing fabric 1620 includes the window 415, and a reverse face 1630 includes diagonal incisions 1640 to fold back. FIG. 17 shows an obverse perspective view 1700 of components for the outer flap 150. These show the window assembly 415 and the separated window flap 220, along with an additional strip 445 that can also serve as the tab 230.

Figure 19:
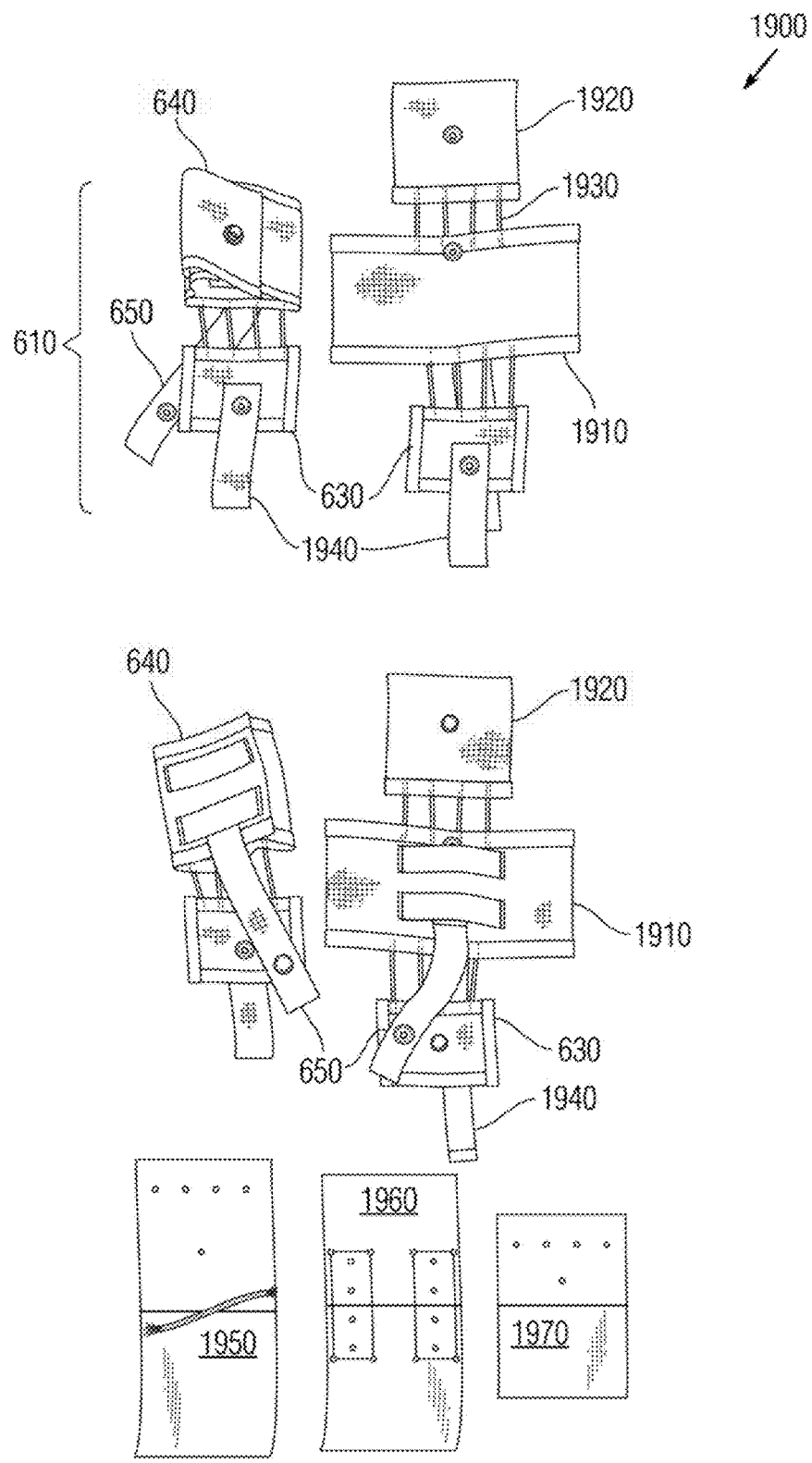
FIG. 19 is a set of perspective views of the external attachments and templates.

FIG. 18 shows an obverse perspective view 1800 of the third pouch 620 including a strap 1810, snap buttons 1820 for folding the ends together and a strip 1830 for inserting writing instruments, such as ink pens. FIG. 19 shows obverse and reverse perspective views 1900 of components of the second pouch 610. The pocket 640 can be unfurled as a strip 1910, which connects to a flap 1920 by cords 1930. Straps 650 and 1940 extend respectively from the pocket 640 and strap 630. Plastic templates 1950, 1960 and 1970 provide stiffening reinforcement for the strip 1910, the flap 1920 and the strap 630.

Figure 20:
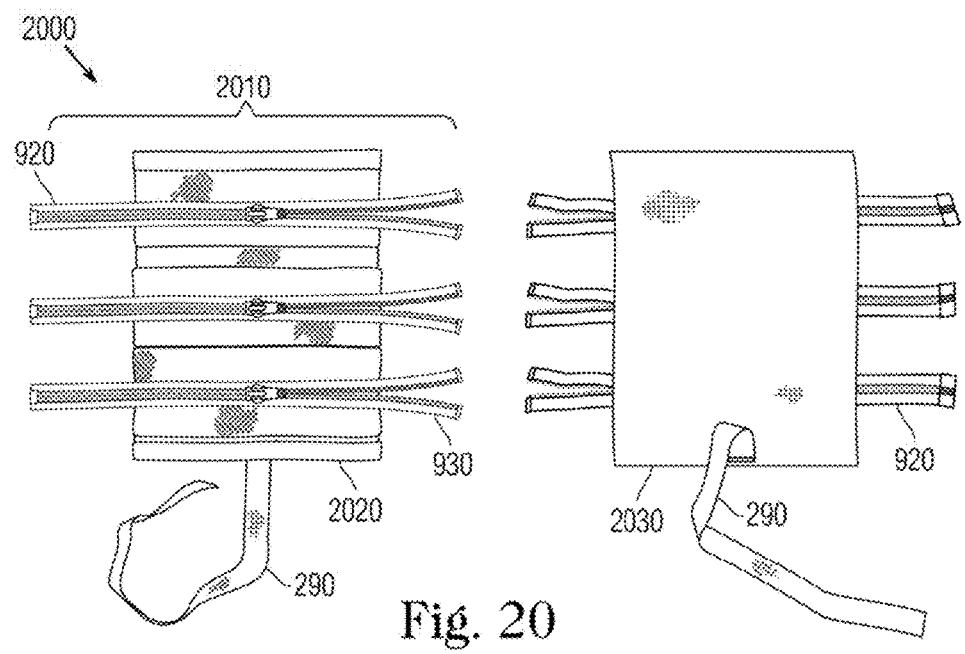
FIG. 20 is set of a perspective views of the utility pocket.

FIG. 20 shows obverse and reverse perspective views 2000 of components 2010 for the utility pocket 170 as further assembly from view 900. An obverse pocket housing 2020 has several seams 320 and extended zippers 920 with clasps 930 that necessitate trimming. A reverse flexible panel 2030 can include a camouflage pattern as well as the strap 290 attached thereto as a tie-down.

Figures 21, 22:
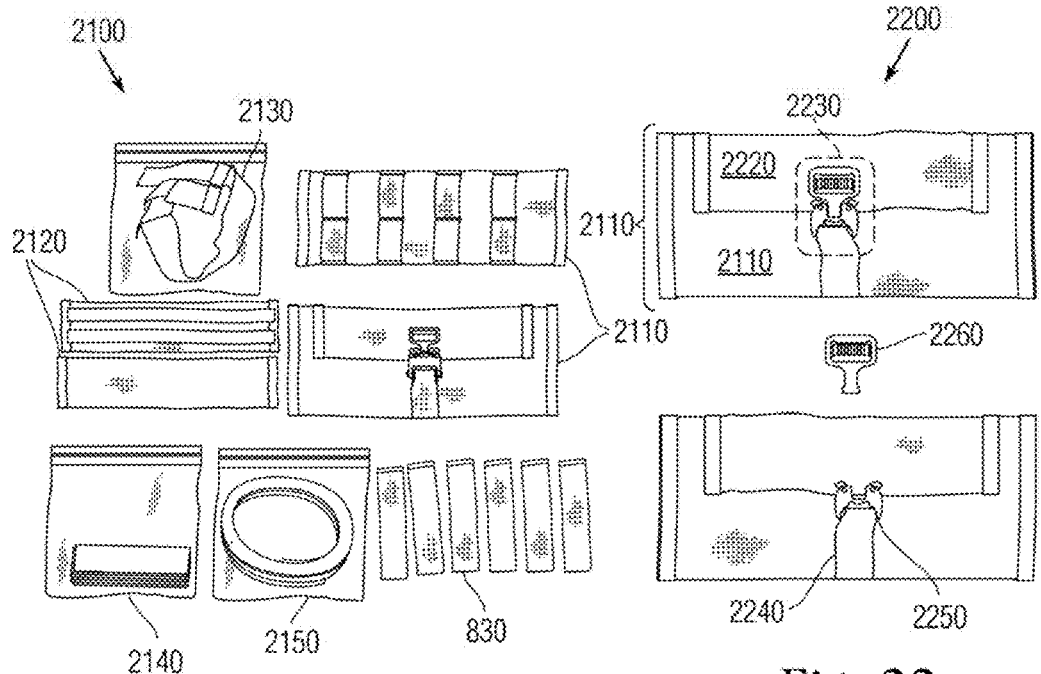
FIG. 21 is a perspective view of straps and MOLLE associated panels.
FIG. 22 is a perspective view of a roll-out pouch locking mechanisms.

FIG. 21 shows obverse and reverse perspective views 2100 of straps and a MOLLE associated panel 2110. The constituents include a strap 2120, MOLLE loop webbing strips 830, MOLLE ribbons 2130, and buckle straps 2140 and 2150 in packages (similar to strips 830 as laid out). FIG. 22 shows reverse views of the panel 2110, which includes a chamber 2210 and a sewn strap 2220 (attached as the strap 2120), but also clasp 2230 attached to a strap 2240 connected to the chamber 2210. The strips 2130 can be used for attaching auxiliary pockets. The clasp 2230 includes a female clevis 2250 that mates to a male tang 2260.

FIGS. 23A, 23B, 23C, 23D, 23E and 23F show various perspective views 2300 of the exemplary bag 120, harness 180 and associated components. As shown in FIGS. 23A and 23C, the bag 120 is suspended by the harness 180 through the grommets 455 and 465 on the respective cowls 160 and 250. In FIGS. 23B and 23F, the inner flap 140 is lowered to expose a clear panel 2310 on the cowl 160 with front window 470 and its side windows 260 flanking the clear panel 2310. In FIGS. 23D and 23E, the outer flap 150 is raised to show the window 415 in front of window 470.

Figure 25:
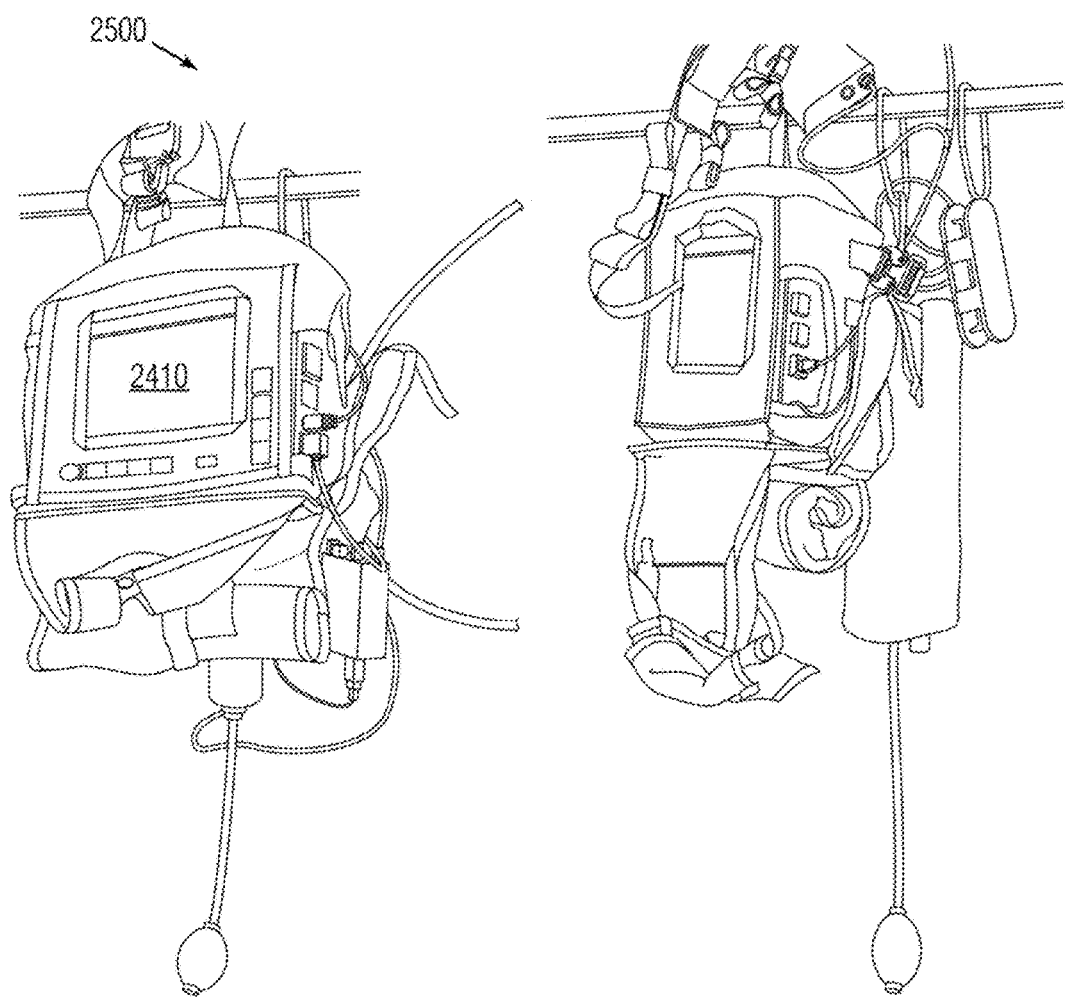
FIG. 25 is a set of perspective views of the bag suspended above a patient bed.

FIG. 24 shows perspective views 2400 of the exemplary satchel 130 and pocket 170 alternatively unfurled and rolled in stowage, as well as a patient monitor 2410 contained within the cowl 160 and visible through the window 260 of the satchel 130. FIG. 25 shows perspective views 2500 of the bag 120 suspended at a field hospital with the monitor 2410 visible through the window 470.

In view 450, the outer front flap 150 includes the window 470 that, open in the middle view, reveal the first pair of abreast grommets 455 on the monitor cowl 160, and the second pair of abreast grommets 465 on the upper cowl 250. The grommets 455 and 465 enable the strap 510 to pass therethrough to secure the monitor 2410 in the satchel 130.

The male button 475 between the first grommets 455 and above the window 415 engages the female button 235 to secure the window flap 220 to the outer front flap 150. The inner transparent panel 2310 with access window 470 of the satchel 130 is revealed with the outer front flap 150 folded towards the utility pocket 170 to facilitate manipulation of controls on the monitor 2410. The MOLLE spine 490 is sewn on the reverse face of the satchel 130 to ventilate the monitor 2410. Straps 290 extend from behind the rear face of the satchel 130.

As the components for the bag 120 are composed of reinforced fabric, end edges for most components feature edge reinforcing seams to inhibit fray damage. Edges sewn to another component lack these seams. For the rear structural panel 710, the top, left and bottom edges are sewn to the front of the satchel 130 or the spine 490 of the satchel 130. For the bottom panel 810, the all four rectangular edges are sewn to the bottom of the satchel 130. For the mesh webbing 910, all four rectangular edges are folded and sewn to the reverse panel 2030, with intermediate seams to form the envelopes 310.

For the cowls 1010 and 1110, the left, bottom and right edges are sewn to the rear upper edge of the satchel 130. For the enclosing panel 1310, the top and bottom edge strips 1320 are sewn to the rear edges of the satchel 130 external to the structural panels 710. For the window assembly 1610, the right edge is sewn to the upper edge of the satchel 130 as the inner flap 140. For the strip 1810 of the third pouch 620, the top edge is sewn to the cowl 160. For the strip 1910 of the second pouch 610, the left and right edges are sewn to join together. For the utility pocket 170, all four edges of the mesh webbing 910 are sewn to the panel 2030, with the top and bottom edges folded and stitched to the panel 2030 to form envelopes 310. For the panel 2110, the top and bottom edges are sewn to the side of the pouch 130, adjacent the monitor cowls 160.

While certain features of the embodiments of the invention have been illustrated as described herein, many modifications, substitutions, changes and equivalents will now occur to those skilled in the art. It is, therefore, to be understood that the appended claims are intended to cover all such modifications and changes as fall within the true spirit of the embodiments.

What is claimed is:

1. A flexible bag for containing a medical monitor attachable to a litter, said bag comprising:
   a housing satchel for receiving the monitor, said satchel receiving the monitor through an upper opening, said satchel having front and rear sides;
   an upper cowl connecting to said satchel for closing said upper opening;
   a first flap connecting to said front side from a bottom edge and secures at a top edge by detachable buttons, said first flap including a window for viewing the monitor;
   a second flap for connecting to said first flap and reversibly covering said window;
   a web mesh on said rear side for ventilation of the monitor; and
   a harness for attaching said satchel to the litter.

2. The bag according to claim 1, wherein said satchel includes flanking side windows for accessing the monitor.

3. The bag according to claim 1, wherein said harness passes through grommets in said upper cowl.

4. A flexible bag for containing a medical monitor attachable to a litter, said bag, comprising:
   a housing satchel for receiving the monitor, said satchel receiving the monitor through an upper opening;
   an upper cowl connecting to said satchel for closing said upper opening;
   a first flap connecting to a front side of said satchel from a bottom edge and secures at a top edge by detachable buttons, said first flap including a window for viewing the monitor;
   a second flap for connecting to said first flap and reversibly covering said window;
   a harness for attaching said satchel to the litter; and
   a utility pocket including a panel that faces aft of said satchel and an envelope having a zipper opening that faces fore of said satchel, said pocket connecting to said satchel at a bottom edge and flexible for rolling underneath said satchel.

5. The bag according to claim 4, wherein said satchel includes flanking side windows for accessing the monitor.

6. The bag according to claim 4, wherein said harness passes through grommets in said upper cowl.

* * * * *